(12) United States Patent
Gruber

(10) Patent No.: US 7,875,137 B2
(45) Date of Patent: Jan. 25, 2011

(54) METHOD FOR APPLYING AND MONITORING AN APPLICATION STRUCTURE COMPRISING A REPAIRING FUNCTION AND DEVICE THEREFORE

(75) Inventor: Bernhard Gruber, Stockdorf (DE)

(73) Assignee: Quiss GmbH, Puchheim (DE)

( * ) Notice: Subject to any disclaimer, the term of this patent is extended or adjusted under 35 U.S.C. 154(b) by 279 days.

(21) Appl. No.: 12/297,630

(22) PCT Filed: Apr. 18, 2007

(86) PCT No.: PCT/EP2007/003398

§ 371 (c)(1),
(2), (4) Date: Oct. 17, 2008

(87) PCT Pub. No.: WO2007/121905

PCT Pub. Date: Nov. 1, 2007

(65) Prior Publication Data

US 2009/0107612 A1    Apr. 30, 2009

(30) Foreign Application Priority Data

Apr. 18, 2006    (DE) ...................... 10 2006 017 956

(51) Int. Cl.
*B32B 41/00*    (2006.01)
(52) U.S. Cl. ........................... 156/64; 156/94; 156/351; 156/356; 156/378
(58) Field of Classification Search .................. 156/64, 156/94, 351, 356, 378; 382/141; 118/665, 118/669
See application file for complete search history.

(56) References Cited

U.S. PATENT DOCUMENTS

| | | | |
|---|---|---|---|
| 6,776,845 B2 * | 8/2004 | Minami et al. | 118/665 |
| 7,364,775 B2 * | 4/2008 | Klein | 427/427.2 |
| 7,488,388 B2 * | 2/2009 | Ryu et al. | 118/664 |
| 7,488,505 B2 * | 2/2009 | Minami et al. | 427/8 |
| 2007/0292629 A1 * | 12/2007 | Linnenkohl et al. | 427/466 |

FOREIGN PATENT DOCUMENTS

WO    WO 96/34273    10/1996
WO    WO 03/021534 A1    3/2003

OTHER PUBLICATIONS

International Search Report for International Application No. PCT/EP2007/003398 dated Jul. 25, 2007, (11) pgs.

* cited by examiner

*Primary Examiner*—George R Koch, III
(74) *Attorney, Agent, or Firm*—Dean D. Small; The Small Patent Law Group

(57) ABSTRACT

A method for applying and monitoring an application structure comprising a repairing function and device thereof are provided. The method includes arranging automatically a first application structure on the substrate using the application device. The first application structure on the substrate monitored by the at least one camera such that the at least one camera is constantly aligned to the first application structure and the first application structure. The method further includes transmitting the images acquired by the at least one camera to an image processing device that analyzes the images of the first application structure and the image processing device filing partial areas of the first application structure. The method also includes applying, after application of all partial areas of the first application structure, at least a second application structure to the substrate by the application device based on the repair list.

16 Claims, 4 Drawing Sheets

METHOD FOR APPLYING AND MONITORING AN APPLICATION STRUCTURE COMPRISING A REPAIRING FUNCTION AND DEVICE THEREFORE

CROSS REFERENCE TO RELATED APPLICATIONS

This application is a filing under 35 U.S.C. §371, which claims priority to PCT Application PCT/EP2007/003398, filed Apr. 18, 2007, and German Application No. DE 10 2006 017 956.0, filed Apr. 18, 2006, which are each hereby incorporated by reference in their entirety.

BACKGROUND OF THE INVENTION

The present invention relates to a method and a device for applying and monitoring at least one application structure, preferably an adhesive bead or adhesive trace, on a substrate with a repairing function.

BRIEF DESCRIPTION OF THE INVENTION

When applying an adhesive bead to a substrate, errors may occur with regard to the position or the width of the adhesive trace or adhesive bead. These errors can be recorded and determined optically by a monitoring device according to the prior art.

In accordance with an embodiment of the invention, a method is provided for applying and monitoring at least one application structure on a substrate, wherein calibration being performed by at least one camera and an application device, prior to applying the application structure. The method includes arranging automatically a first application structure on the substrate using the application device, and the first application structure on the substrate monitored by the at least one camera such that the at least one camera is constantly aligned to the first application structure, and the first application structure, and wherein edges of the adhesive trace around the application device are recorded. The method further includes transmitting the images acquired by the at least one camera to an image processing device that analyzes the images of the first application structure, including analyzing at least one of a width and a position on the substrate, and that classifies substantially each partial area of the first application structure as a partial area not requiring repair or a partial area requiring repair, and the image processing device filing the partial areas of the first application structure requiring repair in a repair list based on the position or the exact displacement path of the application device such that the image processing device constantly assigns the position or the displacement path of the application device to the substrate based on the calibration, such that the image processing device determines and saves the beginning and the end of each partial area of the first application structure requiring repair. The method also includes applying, after application of all partial areas of the first application structure, at least a second application structure to the substrate by the application device based on the repair list, the image processing device transmitting to the application device the beginning and the end of each partial area of the first application structure requiring repair, and thereby controlling the application device such that the second application structure substantially corresponds to the partial areas of the first application structure requiring repair.

In accordance with another embodiment of the invention, an apparatus for applying and monitoring at least one application structure on a substrate is provided. The apparatus includes at least one camera, an application device for applying the application structure, an image processing device for processing the images acquired by the camera(s) and a calibration unit. The calibration unit is configured to perform, prior to applying the application structure by the at least one camera and the application device, arranging automatically a first application structure on the substrate using the application device, and the first application structure on the substrate monitored by the at least one camera such that the at least one camera is constantly aligned to the first application structure, and the first application structure and wherein edges of the adhesive that trace around the application device are recorded. The calibration unit is further configured to perform transmitting the images acquired by the at least one camera to the image processing device that analyzes the images of the first application structure including analyzing at least one of a width and a position on the substrate, and that classifies substantially each partial area of the first application structure as a partial area not requiring repair or a partial area requiring repair, and the image processing device filing the partial areas of the first application structure requiring repair in a repair list based on the position or the exact displacement path of the application device such that the image processing device constantly assigns the position or the displacement path of the application device to the substrate based on the calibration, such that the image processing device determines and saves the beginning and the end of each partial area of the first application structure requiring repair. The calibration unit is further configured to perform applying, after, applying all partial areas of the first application structure, at least a second application structure to the substrate by the application device based on the repair list, the image processing device of the application device transmitting to the application device the beginning and the end of each partial area of the first application structure requiring repair, wherein the application device is controlled such that the second application structure substantially corresponds to the partial areas of the first application structure requiring repair.

BRIEF DESCRIPTION OF THE DRAWINGS

Advantageous embodiments of the invention are illustrated, purely as examples, by means of the following drawings.

DETAILED DESCRIPTION OF THE INVENTION

Figure 1:
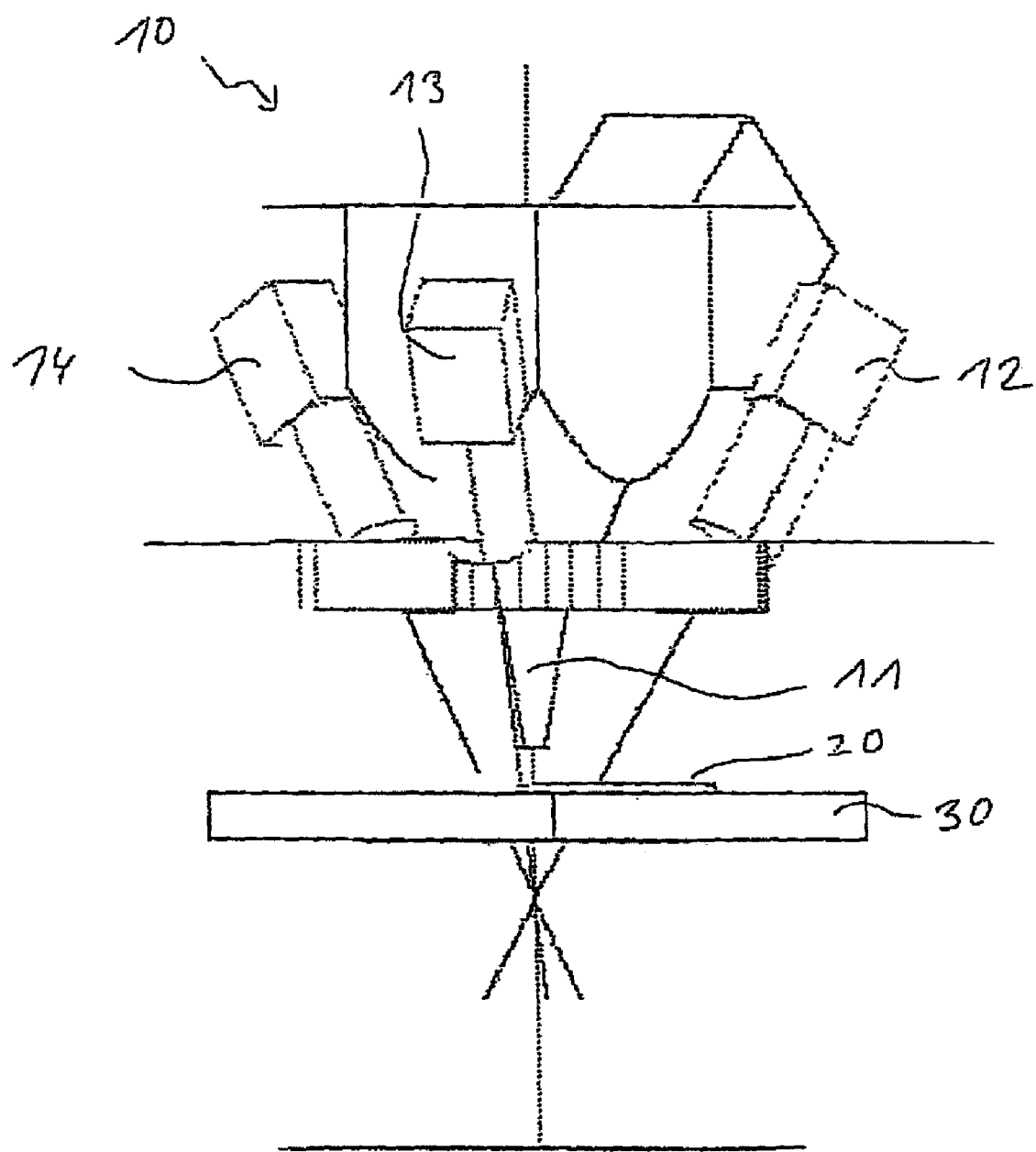
FIG. 1 is a diagram illustrating an exemplary device formed according to various embodiments of the invention for applying and monitoring an application structure.

While the invention has been described in terms of various specific embodiments, those skilled in the art will recognize that the invention can be practiced with modification within the spirit and scope of the claims.

Various embodiments of the invention provide a method for applying and monitoring an application structure with an appropriate repairing function by means of which the errors determined can be corrected. However, with an error correction it is disadvantageous if, after determining an error of the applied adhesive trace, the whole adhesive trace or segments of the adhesive trace must subsequently be applied once again a second time to the substrate. This is in particular because on the one hand the quantity of adhesive comes well over the desired quantity, and on the other hand the application device can cause contamination by means of which further errors are produced and damage can occur to the application device or the component or substrate.

Therefore, various embodiments of the present invention provide a method or a device for applying and monitoring at least one application structure which enables substantially gap-free filling of the errors of a structure or adhesive trace which has already been applied.

In particular, various embodiments of the invention record and determine based errors of the structure applied to the substrate using an image processing device with at least one camera, and which may include using an online method or a stationary camera, with the partial areas requiring repair being filed by the image processing device in a repair list. Immediately after applying the application structure, according to the repair list produced, a second application structure can be applied to the substrate, and for this purpose the image processing device controls the application of the second application structure such that the sum of the initially applied application structure and the second application structure applied during the course of the repair produces the desired application structure or adhesive bead with regard to the path and the width or the volume of the adhesive trace.

In accordance with method of various embodiments, calibration is performed prior to applying the application structure by at least one camera, in particular two or more cameras, and an application device, in order to be able to record the position or the displacement path of the application device in relation to the substrate. A first application structure is subsequently arranged automatically on the substrate by means of the application device, the first application structure being monitored by the camera(s) such that at least one camera is constantly aligned to the first application structure, and the first application structure, in particular the edges of the application structure or adhesive trace, around the application device is recorded. Here the images of the first application structure determined by the camera(s) are transmitted to an image processing device which analyzes the images of the first application structure, at least in accordance with or based on the width and/or the position on the substrate, and which classifies substantially each partial area of the first application structure as a partial area not requiring repair or requiring repair. The image processing device subsequently files the partial areas of the first application structure requiring repair in accordance with the position or the exact displacement path of the application device in a repair list such that the image processing device constantly assigns the position or the displacement path of the application device to the substrate upon the basis of the calibration so that the image processing device determines and saves the beginning and the end of each partial area of the first application structure requiring repair. After applying the whole first application structure or all partial areas of the first application structure, at least a second application structure is subsequently applied to the substrate by the application device in accordance with or based on the repair list, the image processing device of the application device transmitting the beginning and the end of each partial area of the first application structure requiring repair, and in this way controlling the application device such that the second application structure substantially corresponds to the partial area(s) of the first application structure requiring repair.

For the method according to various embodiments of the invention, a single camera is used particularly if a path of an adhesive trace or application structure substantially in a straight line or only slightly curved is to be monitored. If, however, a strongly curved path of an application structure is to be examined, two or more cameras may be used. For the monitoring, the one or more cameras can be attached to the application device or a robot or can be disposed stationarily.

A method for applying and monitoring an application structure with a repairing function is thus provided which enables gap-free completion of the first application structure or adhesive trace, by means of which an appropriate error correction or repair function for applying the application structure or adhesive trace is made possible.

It is advantageous if the repair list is produced in accordance with or based on the position or the displacement path of the application device, for this purpose in particular the information regarding the path covered by the application device being used.

According to some embodiments of the invention, the partial areas of the first application structure requiring repair are defined for the repair list in accordance with or based on the beginning and the end of the displacement time of the application device.

Furthermore, it is advantageous if the image processing device transmits the path and/or the width of the second application structure to the application device by means of the repair list dependently upon the path and/or the width of the first application structure. In connection with this it should be mentioned that the application device can control and comprise both a controllable metering device, for example for the adhesive discharge, and a robot for the displacement path. Consequently, after recording the error—whether the trace path is incorrect or if the width of the adhesive trace is insufficient—the first application structure can be corrected by the image processing device in accordance with a pre-specified reference value.

If the repair list is produced in the form of a data table, which includes at the very least the number of partial areas of the first application structure requiring repair, the measuring unit for the position of the partial areas requiring repair, the duration and/or the length of the partial areas requiring repair, and/or the width of the partial areas of the first application structure requiring repair, the relevant data for the required repair can be filed in an appropriate form and further processed by the image processing device. This data table is subsequently used for controlling the application device for the second application structure, in particular with the aid of the calibration implemented at the start of a corresponding displacement path and corresponding control of the application nozzle of the image processing device being calculated.

According to one preferred embodiment of the invention, the second application structure is applied by the application device such that the application device moves a pre-specified distance away from the substrate to the beginning of the partial area of the first application structure requiring repair, and at the beginning of the partial area requiring repair moves to the substrate for application of the second application structure, and at the end of the application of the second application structure moves away from the substrate. For this purpose the application device can be moved by a specific amount within the tool coordinate system contrary to the approach movement of the application device or upwardly so that the now prepared application track is moved away from by a specific amount over the component or substrate, and cannot come into contact with the adhesive.

Moreover, at the beginning and at the end of application of the second application structure, an offset in relation to the partial area of the first application structure requiring repair can be implemented, which can be defined by the image processing device. The repair application and the second application structure can thus be implemented before and after the beginning and the end of the determined error. The advantage of this is that the inaction of the valves or the mechanism can be compensated by the temporal offset or a spatial offset if, for example, the signal defines 5 mm or a split second before the start of the gap for opening the valve of the application device. Furthermore, the offset can also be implemented by the application device itself, which in relation to the control elements, for example the valves, has a pre-defined inaction, and so a corresponding offset.

If for applying the second application structure the application device has an angle of inclination in relation to the first application with the application and displacement path for the second application structure, when moving away for the repair application the application device can be moved not only in the z direction or upwardly, i.e. perpendicularly to the component surface or to the substrate, but also be at least partially offset in the x, y direction or at the inclination. In this way the application device for the second application structure can be moved more closely past the already existing first application structure, making it possible to apply the second application structure to the substrate particularly quickly.

According to various embodiments, for applying the second application structure, the application device moves away from the displacement path of the first application structure. Here, after applying the first application structure, the application device can apply the second application structure directly, as it were, in reverse or in the same way as the first application.

Furthermore, for applying the second application structure, the application device can move directly into the position or up to the position of the beginning of the partial area requiring repair in order to minimize the duration of the repair application because the corresponding position of the image processing is known upon the basis of the calibration.

Furthermore, for applying the second application structure, the speed of the application device can be varied. This adjustable parameter is advantageous in particular for repair with spray-on adhesive in order to reduce the speed with which the application device moves away from the repair path when filling gaps.

According to a further aspect of the invention, a device is provided for implementing the methods of the various embodiments, which comprises at least one camera, in particular two or more cameras, an application device for applying the application structure, and an image processing device for the images determined by the camera(s), calibration being performed prior to applying the application structure by the camera(s) and the application device, a first application structure being automatically arranged on the substrate by means of the application device, and the first application structure on the substrate being monitored by the camera(s) such that at least one camera is constantly aligned to the first application structure, and the first application structure, in particular the edges of the adhesive trace, around the application device is recorded; and the images determined by the camera(s) being transmitted to an image processing device, which analyzes the images of the first application structure at least in accordance with or based on the width and/or the position on the substrate; and which classifies substantially each partial area of the first application structure as a partial area not requiring repair or a partial area requiring repair, and the image processing device filing the partial areas of the first application structure requiring repair in a repair list in accordance with or based on the position or the exact displacement path of the application device such that the image processing device constantly assigns the position or the displacement path of the application device to the substrate upon the basis of the calibration so that the image processing device determines and saves the beginning and the end of each partial area of the first application structure requiring repair, after applying all partial areas of the first application structure, at least a second application structure subsequently being applied to the substrate by the application device in accordance with or based on the repair list, the image processing device transmitting to the application device the beginning and the end of each partial area of the first application structure requiring repair, and in this way the application device being controlled such that the second application structure substantially corresponds to the partial areas of the first application structure requiring repair.

With the various embodiments of methods for applying and monitoring at least one application structure or an adhesive trace, a device is used which is illustrated, for example, in FIG. 1.

According to FIG. 1, reference number 10 shows the diagrammatically illustrated device for applying and identifying an adhesive trace. An application device 11 is disposed in the center of the apparatus by means of which an adhesive trace 20 is applied from right to left to a substrate or a metal sheet 30 in FIG. 1. Three cameras 12, 13, 14 are disposed at equal distances in a circle around the application device 11. However, more or less cameras may be used. During the adhesive inspection, the application device is either moved with the cameras or the substrate, at the same time the adhesive trace 20 being applied to the substrate 30 by means of the application device 11, and the cameras 12, 13, 14 monitoring the applied structure.

Furthermore, the cameras are connected to an image processing device. The device of FIG. 1 is described in particular in the published PCT application WO 2005/063407 to which reference is made with regard to the online monitoring of the adhesive application, and which is hereby incorporated by reference in its entirety.

When identifying the application structure, the edges of the adhesive trace on a peripheral path around the application device are determined, with the peripheral path being defined such that after application, the application structure intersects the peripheral path, and the cameras monitoring the application structure, in particular forming a circle caliper, and collectively form a global coordinate system. Here a segment of the circular path with respect to adjacent overlap regions is assigned to the images of the individual cameras.

This type of device for applying and identifying an adhesive trace is calibrated prior to application, as described for example according to the aforementioned WO 2005/063407 to which reference is made with regard to the calibration and the device. With regard to the online monitoring with a high-frequency analysis reference is also made to WO 2005/063406.

Figure 2:
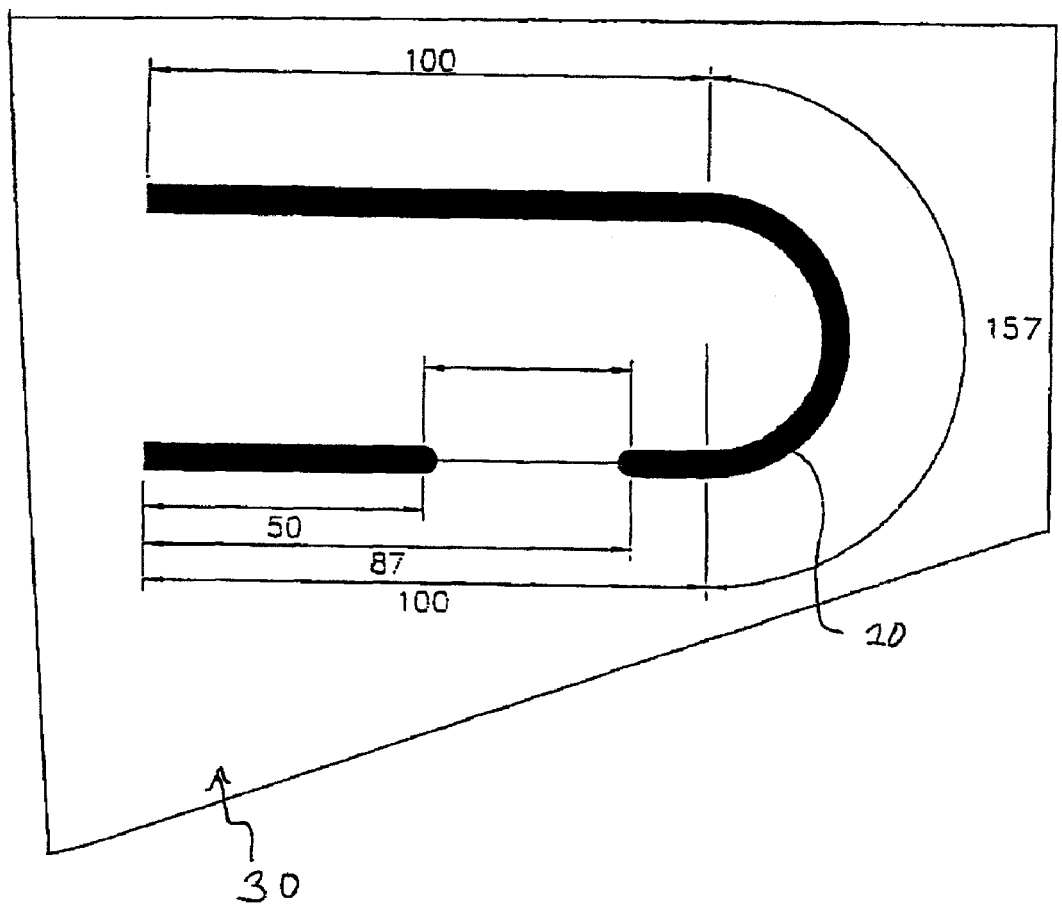
FIG. 2 shows a first application structure or adhesive trace which has been applied to a substrate by the application device.

In FIG. 2 a first application structure 20, which has been applied to the substrate 30 by the application device is now shown as an example. Here the cameras are aligned to the first application structure 20 and are recorded by the latter and transmitted to an image processing device. During application of the first application structure 20, the image processing device analyzes the images of the cameras in accordance with or based on the width and/or the position of the first application structure and for each partial area calculates whether this is a partial area requiring repair or not.

According to FIG. 2 it is shown in particular that there is no partial area requiring repair for the first 50 mm, adjacent to this however up to 87 mm displacement path of the application device, therefore a gap of 37 mm. For this partial area of 37 mm of the first application structure a repair is therefore necessary. The further remaining path of the first application structure 20 does not have any errors. According to various embodiments, the error of the first application structure should be corrected.

In order to now correct the faulty 37 mm of the first application structure 20, with the online monitoring of the first application structure according to the displacement path of the application device, a repair list is already produced by the image processing device with regard to the partial areas requiring repair. In the current case, the 37 mm long partial area requiring repair is filed in this repair list, the width of the first application structure being 0 mm, i.e. there is a gap of 37 mm.

By calibrating the application device and the cameras, it is possible for the image processing device that after application of the first application structure, a second repair application in accordance with or based on the repair list or a second application structure is applied. For this purpose, the image processing device transmits to the application device the beginning of the partial area requiring repair 50 mm after the start of the application path and the end of 87 mm. According to the details provided by the image processing device from the repair list, the application device implements a second application structure by precise filling of the gaps and inserts a 37 mm long second application structure or adhesive trace into the gap so that a uniform application structure is produced which is made up of the first and second application structures.

As stated previously, the control of the application device or of an application nozzle and of corresponding valves for the adhesive application is provided by the image processing. The image processing passes on the local information regarding the gap to the robot or to the application device which subsequently controls the second adhesive application. By means of the repair list or the sequence list, the error can be clearly assigned to the robot path, i.e. in accordance with the displacement path the gap has occurred after 50 mm with a length of 30 mm. By means of online monitoring this error can be processed directly after application or after the total first application movement.

Upon the basis of the calibration with the method according to various embodiments of the invention, the image processing constantly has the information regarding at which location the application device or the sensor is located at any time with respect to the displacement path. Furthermore however, the beginning of the gap and the end of the gap can be defined by the time when the application device covers the displacement path in the same time, in particular at constant speed. Therefore, the beginning of the error can be defined by a time value in milliseconds with which an error or a gap or an excessively narrow adhesive trace starts if one starts from the starting point of the adhesive application. Alternatively, the start of the error can, as explained, also be recorded in millimeters. The error duration or the time duration in milliseconds of the detected error, i.e. the gap or the excessively narrow bead, can likewise be shown in millimeters.

According to an error with regard to the bead width, the minimum, maximum and average bead width can be classified in millimeters in the error range detected. Furthermore, a percentage bead width can be used with regard to the actual value and the desired value. According to various embodiments of the invention, the image processing can select whether the error values are provided as a time or length value.

All of the errors and partial areas requiring repair are included in the repair list with the image processing being able to provide specific data to a superior control for the application device. As described above, after the conclusion of the examination the data should be provided in the form of a data table or repair list. The data table starts with a header and contains information about the number of gaps, the measuring units for the gap position, the gap duration or gap length and the adhesive seam width. Furthermore, a plurality of reserve spaces, for example, two reserve spaces, can be provided.

Figure 3:
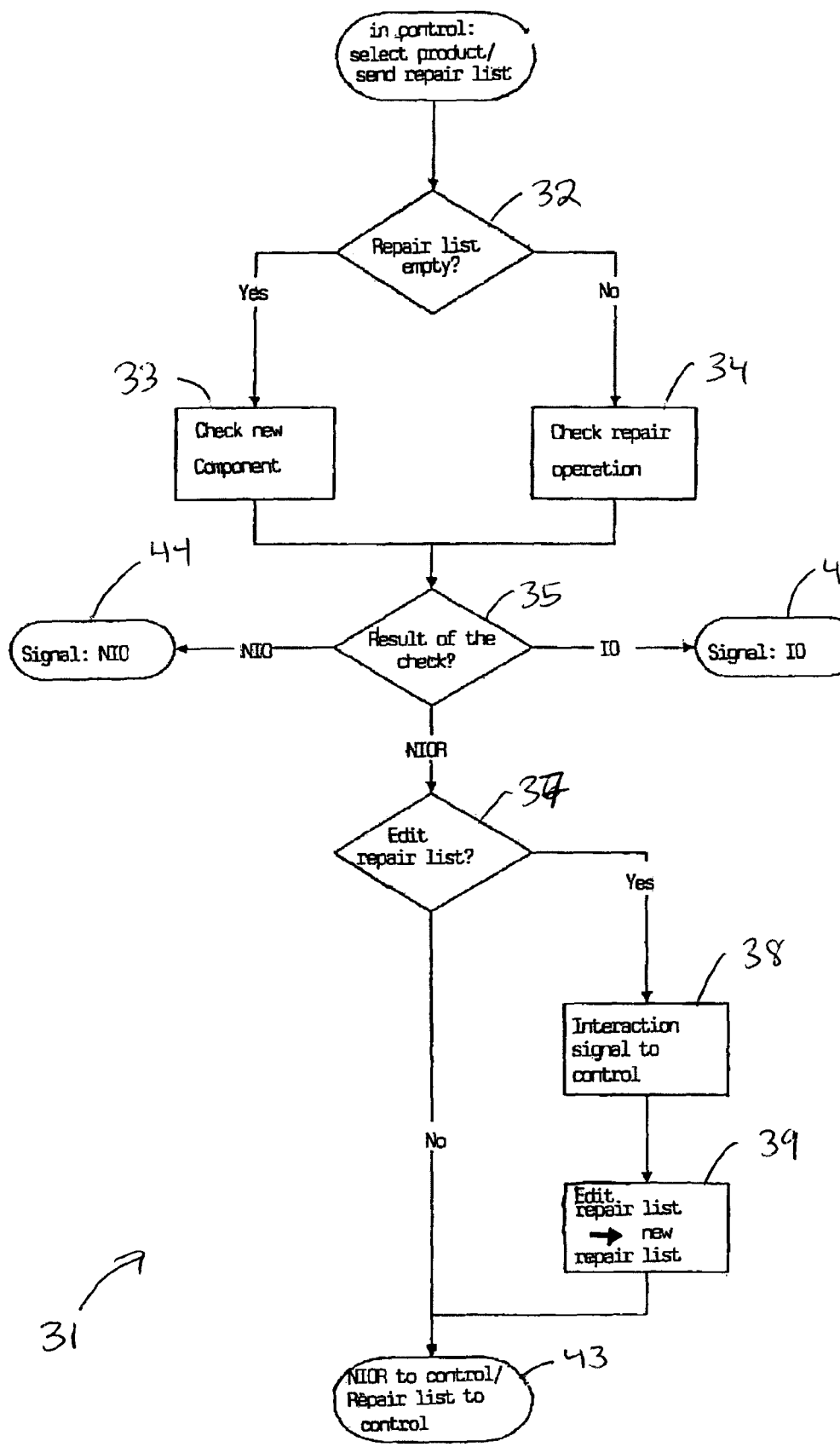
FIG. 3 is a flowchart of a method for performing a repairing function in accordance with various embodiments of the invention.

According to FIG. 3, an adhesive application inspection method 31 is shown. After application of the first adhesive trace, a check is performed at 32 as to whether the repair list is empty or not. If the repair list is empty, at 33 a new component is examined or a first adhesive application to a new component is implemented. If the repair list is not empty, a repair operation is checked at 34. According to this result the repair list is edited, and a corresponding inspection signal is sent to the control at 35.

If the image processing device signals a NIOR (repairable incorrect) (as opposed to a NIO at 44 or an IO at 45), there must optionally be the possibility at 37 of editing the errors entered in the repair list, i.e. to eliminate the errors totally from the list at 38 and 39, otherwise the method proceeds to 43.

The parameters required for the configuration of the automatic repair of adhesive and sealant beads should be defined for each area. For this purpose the following values should be inputted. In the area characteristics an "repair definition" rider is provided in addition to the "area definition", "error definition" and "adhesive definition" riders. This relates to the length of the adhesive gap in millimeters as from which an error signal is sent to the control, i.e. that an entry is made in the repair list. Furthermore, the width of the bead is specified in millimeters as from which an error signal is sent to the control, i.e. that a corresponding entry is made in the repair list. Furthermore, a displacement or an offset can be specified in millimeters by how much a repair application should apply before or after the start of the error. In the same way as this, a displacement or an offset can be entered in millimeters by how much a repair application is to be ended before or after the end of the error.

Furthermore, it can be entered whether a repair operation is to be checked and by what percentage the error and warning limits are to be extended. The error definitions of the values provided for the individual areas serve as a basis for this. This detail is provided in the area definition of additional "repair definition" riders.

Furthermore, parameters with regard to the inspection characteristics can be provided with a "repair" rider in addition to the "image source", "reference" and "areas" riders in the set-up mode. Here the total length is entered in millimeters of the errors, i.e. gaps and/or a faulty width of the adhesive trace as from which no repair needs to be made i.e. that no error to be repaired is indicated either, but only still NIO.

Figure 4:
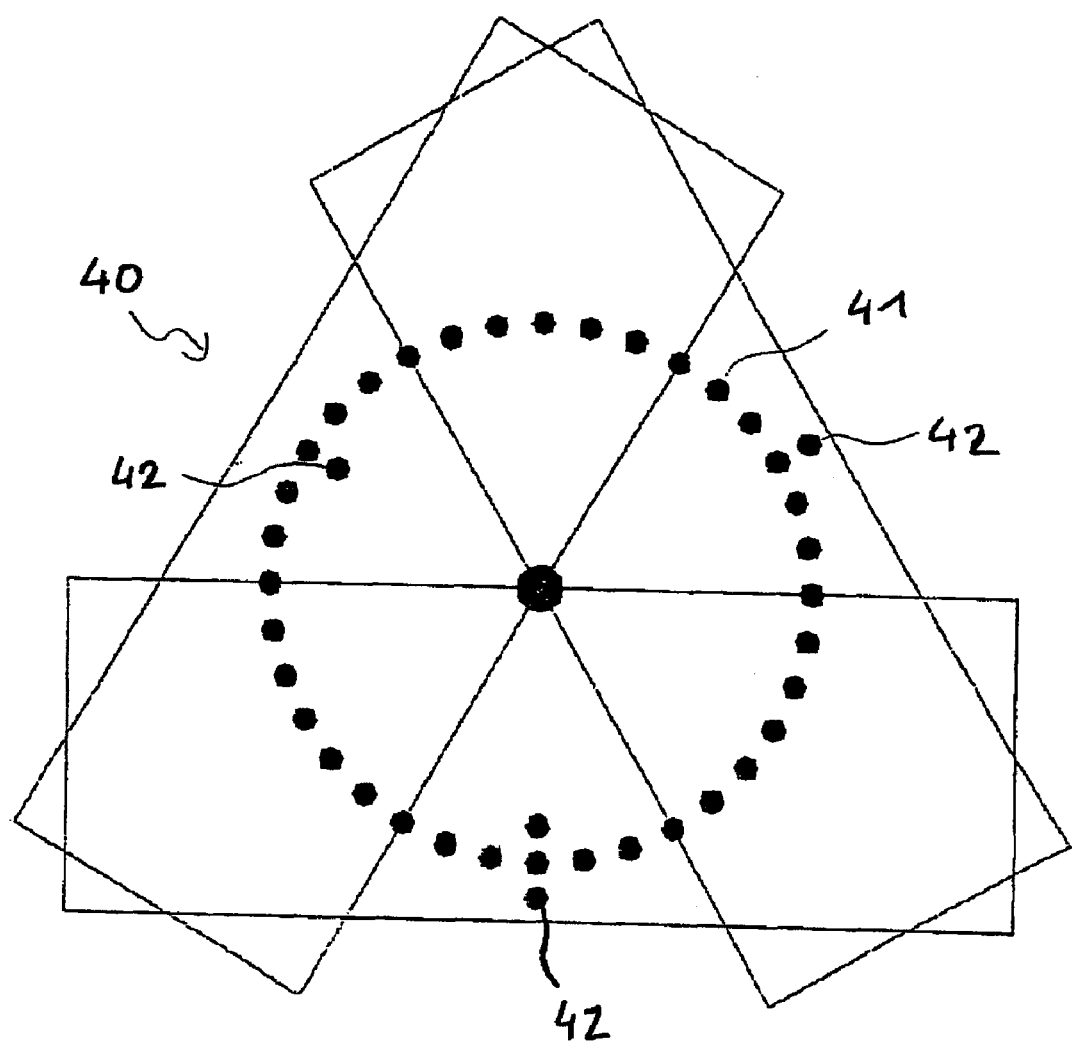
FIG. 4 is a diagram that shows a calibration device for calibrating the individual cameras in accordance with various embodiments of the invention.

According to FIG. 4, a calibration device 40 is shown which is used for calibrating the one camera or number of cameras of the device according to various embodiments of the invention, and if appropriate the application device, and so can be correspondingly controlled by the image processing device. Upon the basis of the calibration the cameras are also assigned and calibrated to one another so that the image processing device can respectively assign the images from different cameras of the application structure upon the basis of the monitoring of individual cameras. In particular, upon the basis of the calibration, it is possible for the image processing for the individual pixels of the cameras to be recorded in millimeters.

The calibration device 40 in the example shown in FIG. 4 is designed for three cameras, the monitoring range of which is shown by corresponding rectangular strips. For this purpose the calibration device 40 comprises a circular calibration disc in order to assign its scaling factor, its angular affinity and the center point and the radius of its search circle to the individual cameras.

The calibration disc comprises individual form elements disposed on a circular path or dots 41 which are respectively disposed with angular spacing of substantially 10°. Furthermore, marking points 42 are disposed at the same distance from one another in order to calibrate three cameras. By means of an adjustment calculation on the one hand, the scaling factor of the individual cameras, and on the other hand the center point and the radius of the search area are calculated from the coordinates of the center points of the individual dots. By means of the marking points at angles of 0°, 120°, 240° in the global coordinate system, the angle allocation and the respective field of vision of the individual cameras can be determined. The field of vision of the individual cameras is shown in particular by the three rectangles in FIG. 4, the form elements 41 of the circular path of the circular caliper being able to correspond to the recording of the adhesive trace.

Therefore, a method and a device for applying and monitoring at least one application structure, for example, an adhesive bead or adhesive trace, on a substrate are described, with calibration being performed prior to applying the application structure by at least one camera, and in particular two or more cameras, and an application device, a first application structure being arranged automatically on the substrate by means of the application device, and the first application structure on the substrate being monitored by the camera(s) such that at least one camera is aligned to the first application structure; and the first application structure, in particular the edges of the adhesive trace, around the application device is recorded, and the images determined by the camera(s) being transmitted to an image processing device which analyzes the images of the first application structure, at least in accordance with or based on the width and/or the position on the substrate; and which classifies substantially each partial area of the first application structure as a partial area not requiring repair or a partial area requiring repair, and the image processing device filing the partial areas of the first application structure requiring repair in accordance with or based on the position or the exact displacement path of the application device in a repair list such that the image processing device constantly assigns the position or the displacement path of the application device to the substrate upon the basis of the calibration so that the image processing device determines and saves the beginning and the end of each partial area of the first application structure requiring repair, after application of all partial areas of the first application structure subsequently, in accordance with or based on the repair list, with at least a second application structure being applied to the substrate by the application device, the image processing device of the application device transmitting the beginning and the end of each partial area of the first application structure requiring repair, and in this way the application device being controlled such that the second application structure substantially corresponds to the partial area(s) of the first application structure requiring repair.

The invention claimed is:

1. A method for applying and monitoring at least one application structure on a substrate, wherein calibration being performed by at least one camera and an application device, prior to applying the application structure, the method comprising:

arranging automatically a first application structure on the substrate using the application device, and the first application structure on the substrate monitored by the at least one camera such that the at least one camera is constantly aligned to the first application structure, and the first application structure, and wherein edges of the adhesive trace around the application device are recorded;

transmitting the images acquired by the at least one camera to an image processing device that analyzes the images of the first application structure, including analyzing at least one of a width and a position on the substrate, and that classifies substantially each partial area of the first application structure as a partial area not requiring repair or a partial area requiring repair, and the image processing device filing the partial areas of the first application structure requiring repair in a repair list based on the position or the exact displacement path of the application device such that the image processing device constantly assigns the position or the displacement path of the application device to the substrate based on the calibration, such that the image processing device determines and saves the beginning and the end of each partial area of the first application structure requiring repair; and applying, after application of all partial areas of the first application structure, at least a second application structure to the substrate by the application device based on the repair list, the image processing device transmitting to the application device the beginning and the end of each partial area of the first application structure requiring repair, and thereby controlling the application device such that the second application structure substantially corresponds to the partial areas of the first application structure requiring repair.

2. The method according to claim 1, wherein the repair list is produced based on the position or the displacement path of the application device, and further comprising using the information regarding the path covered by the application device for producing the repair list.

3. The method according to claim 1, wherein the partial areas of the first application structure requiring repair are defined for the repair list based on the beginning and the end of the displacement time of the application device.

4. The method according to claim 1, wherein the image processing device transmits at least one of the path and the width of the second application structure to the application device using the repair list and dependent on the path or the width of the first application structure.

5. The method according to claim 1, wherein the repair list comprises a data table that includes at least one of the number of partial areas of the first application structure requiring repair, measuring units for the position of the partial areas requiring repair, at least one of a duration and the length of the partial regions requiring repair, and the width of the partial areas of the first application structure requiring repair.

6. The method according to claim 1, wherein the second application structure is applied by the application device such that the application device moves a pre-specified distance away from the substrate to the beginning of the partial area of the first application structure requiring repair and at the beginning of the partial area requiring repair moves to the substrate for application of the second application structure, and at the end of the application of the application structure moves away from the substrate.

7. The method according to claim 1, wherein at the beginning and at the end of application of the second application structure, further comprising applying an offset in relation to the partial area of the first application structure requiring repair is implemented which can be defined by the image processing device.

8. The method according to claim 1, wherein when applying the second application structure, the application device includes an angle of inclination in relation to the first application with the application and displacement path for the second application structure.

9. The method according to claim 1, wherein when applying the second application structure, the application device moves away from the displacement path of the first application structure.

10. The method according to claim 1, wherein when applying the second application structure, the application device moves directly into the position of the beginning of the partial area requiring repair.

11. The method according to claim 1, further comprising varying a speed of the application device for the application of the second application structure.

12. The method according to claim 1, wherein the application structure comprises one of an adhesive bead and an adhesive trace.

13. The method according to claim 1 comprising at least two cameras.

14. An apparatus for applying and monitoring at least one application structure on a substrate, the apparatus comprising at least one camera;

an application device for applying the application structure;

an image processing device for processing the images acquired by the camera(s); and a calibration unit configured to perform, prior to applying the application structure by the at least one camera and the application device:

arranging automatically a first application structure on the substrate using the application device, and the first application structure on the substrate monitored by the at least one camera such that the at least one camera is constantly aligned to the first application structure, and the first application structure and wherein edges of the adhesive that trace around the application device are recorded;

transmitting the images acquired by the at least one camera to the image processing device that analyzes the images of the first application structure including analyzing at least one of a width and a position on the substrate, and that classifies substantially each partial area of the first application structure as a partial area not requiring repair or a partial area requiring repair, and the image processing device filing the partial areas of the first application structure requiring repair in a repair list based on the position or the exact displacement path of the application device such that the image processing device constantly assigns the position or the displacement path of the application device to the substrate based on the calibration, such that the image processing device determines and saves the beginning and the end of each partial area of the first application structure requiring repair;

applying, after, applying all partial areas of the first application structure, at least a second application structure to the substrate by the application device based on the repair list, the image processing device of the application device transmitting to the application device the beginning and the end of each partial area of the first application structure requiring repair, wherein the application device is controlled such that the second application structure substantially corresponds to the partial areas of the first application structure requiring repair.

15. The apparatus of claim 14 wherein the application structure comprises one of an adhesive bead and an adhesive trace.

16. The apparatus of claim 14 comprising at least two cameras.

* * * * *